(12) United States Patent
Gu et al.

(10) Patent No.: US 9,664,601 B1
(45) Date of Patent: May 30, 2017

(54) PRE-TREATMENT METHOD FOR DETERMINATION OF VOLATILE THIO-ETHER COMPOUNDS IN OFFENSIVE ODOROUS SEDIMENT

(71) Applicants: Nanjing Institute of Geography&Limnology. Chinese Academy of Sciences, Nanjing (CN); Ji Shen, Nanjing (CN)

(72) Inventors: Xiaozhi Gu, Nanjing (CN); Kaining Chen, Nanjing (CN); Shuyun Sun, Nanjing (CN); Miao Liu, Nanjing (CN); Jia Kang, Nanjing (CN); Yadong Wang, Nanjing (CN)

(73) Assignee: Nanjing Institute of Geography & Limnology, Chinese Academy of Sciences, Nanjing, Jiangsu (CN)

( * ) Notice: Subject to any disclaimer, the term of this patent is extended or adjusted under 35 U.S.C. 154(b) by 0 days.

(21) Appl. No.: 15/096,281

(22) Filed: Apr. 12, 2016

(30) Foreign Application Priority Data

Nov. 23, 2015  (CN) .......................... 2015 1 0819428

(51) Int. Cl.
| | |
|---|---|
| G01N 33/24 | (2006.01) |
| G01N 1/18 | (2006.01) |
| G01N 1/34 | (2006.01) |
| G01N 1/40 | (2006.01) |
| G01N 1/42 | (2006.01) |
| G01N 33/18 | (2006.01) |
| A61L 2/18 | (2006.01) |
| G01N 33/00 | (2006.01) |

(52) U.S. Cl.
CPC ............... *G01N 1/34* (2013.01); *G01N 1/405* (2013.01); *G01N 1/4044* (2013.01); *G01N 1/4077* (2013.01); *G01N 1/42* (2013.01); *G01N 33/18* (2013.01); *G01N 33/24* (2013.01); *A61L 2/18* (2013.01); *G01N 33/0044* (2013.01); *G01N 2001/4094* (2013.01); *Y10T 436/182* (2015.01); *Y10T 436/25* (2015.01); *Y10T 436/255* (2015.01); *Y10T 436/25125* (2015.01)

(58) Field of Classification Search
CPC .. G01N 33/0044; G01N 33/24; Y10T 436/18; Y10T 436/182; Y10T 436/25; Y10T 436/25125; Y10T 436/25375; Y10T 436/255
USPC ... 436/25, 31, 119, 120, 161, 174, 175, 177, 436/178
See application file for complete search history.

(56) References Cited

PUBLICATIONS

Kristiana et al. Journal of Chromatography A, vol. 1217, Jul. 22, 2010, pp. 5995-6001.*

* cited by examiner

*Primary Examiner* — Maureen Wallenhorst
(74) *Attorney, Agent, or Firm* — Bei & Ocean; George G. Wang

(57) ABSTRACT

Method for determining volatile thio-ether compounds in offensive odorous sediment including: pre-treating a sediment sample, extracting volatile thio-ether compounds, separating and purifying the extraction supernatant in a solid phase extraction column, eluting with ethyl acetate, and finally collecting the eluent, which is then concentrated and used for determination by gas chromatography.

8 Claims, 3 Drawing Sheets

PRE-TREATMENT METHOD FOR DETERMINATION OF VOLATILE THIO-ETHER COMPOUNDS IN OFFENSIVE ODOROUS SEDIMENT

CROSS-REFERENCE TO RELATED APPLICATIONS

This application claims priority from CN Application No. 201510819428.3, filed Nov. 23, 2015, the contents of which are incorporated herein in the entirety by reference.

FIELD OF THE INVENTION

The invention belongs to the field of environmental protection technology, and specifically to a pre-treatment method for the determination of volatile thio-ether compounds in offensive odorous sediment.

BACKGROUND OF THE INVENTION

At present, with respect to the problem of black and odorous water body occurring in city river beds and local lake areas in China, but the focuses of pre-treatment technique related to volatile thio-ether compounds in the water body are on water body, biological samples such as fish. Patent 201120511340.2 has mentioned a determination method, comprising accelerating volatilization of dimethyl trisulfide in the sediment by microwave heating method, and then collecting volatilized odorous gas compounds by purging and trapping. The largest disadvantage of this method is over-emphasis on qualitative analysis of odorous compounds, only a part of weak absorbed dimethyl trisulfide compound in the sediment is resolved and then collected for determination, and most of the compound still resides in the sediment. In addition, as the main component of lake ecosystem, the sediment contains sulfur-containing compounds, which produce a large amount of sulfur-containing compounds during biological environmental geochemical cycling in the earth's crust, and except dimethyl trisulfide, these compounds like dimethyl sulfide, dimethyl trisulfide, dimethyl disulfide, etc. are important odorous compounds in the water body. It is reported in literature that Taihu lake water crisis in 2007 is mainly due to water body smelliness caused by excessively high content of dimethyl trisulfide and dimethyl disulfide. Except that a part of volatile thio-ether compound is produced by putrefaction and decomposition of algae, most of volatile thio-ether compounds are from diffusion and release of sediment into overlying water body. Therefore it is crucial to grasp environmental information of thio-ethers in the sediment.

With further research work, acquiring content and categories of volatile thio-ether compounds in the sediment simply by qualitative or semi-quantitative method cannot satisfy the requirement for accurately learning environmental geochemical information of volatile thio-ether compounds at the sediment-water interface. Need for a rapid and accurate extraction method of volatile thio-ether compounds in the sediment in related analytic chemistry work has become the restrictive bottle neck of thio-ether compound research at present; it is of great scientific and technical significance to grasp the rapid and accurate pre-treatment method for further study of environmental geochemical behaviors of volatile thio-ether compounds in lake water body, and the diffusion mechanism at the sediment-water interface for scientifically guiding treatment of black and odorous water body.

SUMMARY OF THE INVENTION

The invention aims at providing a pre-treatment method for determining thio-ether volatile compounds in sediment, and said pre-treatment method for determining volatile thio-ether compounds is applied to rapid detection of categories and content of odorous compounds in local anaerobic water body and bottom mud in lake, reservoir or river bed.

In order to achieve above objective, the invention employs the following technical schemes:

a pre-treatment method for the determination of volatile thio-ether compounds in offensive odorous sediment, said method comprising the following steps:

(1) Sample collection and sealed storage away from light: collecting a cylindrical core sample of fresh sediment from a lake or river bed by a sediment corer and retaining a water column of certain length, and removing stones, animal and plant residues such as snails, *corbicula fluminea* and plant root system in the sludge sample; collecting a plurality of fresh sludge samples therein, rapidly filling into a brown glass bottle and retaining water of about 1 cm, and then sealing.

(2) Sample refreshing and anaerobic pre-treatment: adding 0.1% $HgCl_2$ to the surface of fresh sediment for sterilization, adding certain amount of dry ice at the same time, keeping the sample refrigerated, while creating an anaerobic environment on the surface of sediment; and finally placing a brown sample bottle into a liquid nitrogen container for cold storage, and transporting back to laboratory in time for determination.

(3) Volatile thio-ether compound extraction: compound extraction being two-step continuous extraction, comprising alcohol/water exchange step in the first step and ultrasonic extraction with mixed extractant in the second step.

The first step: alcohol/water exchange: first weighing some sediment sample in a centrifuge tube, adding absolute methanol and NaCl at a certain solid-to-liquid ratio, shaking adequately, then centrifuging and collecting supernatant after standing still, repeating three times, and finally combing supernatant extracted three times above for use.

The second step: ultrasonic extraction with mixed extractant: adding mixed extraction solution of methanol/cyclohexane to a residual sludge sample extracted in the first step at a certain solid-to-liquid ratio, then performing ultrasonic extraction in an ultrasonic cell disruption instrument at a certain temperature, continuously repeating three times, and finally combing ultrasonic extract obtained three times for use.

(4) Purification of sediment extract: collecting and combing the extract obtained in the first step and the second step, then separating and purifying impurities in the extract in the solid phase extraction column at a certain flow rate; and finally eluting with ethyl acetate solution, collecting the eluent and concentrating on a rotary evaporator for determination.

(5) Sample determination: determining the concentrated solution to be determined on a chromatograph, and for specific detection parameter setting of the instrument and requirements for sample loading, refer to sample determination of volatile thio-ether compounds in water body.

Water column of certain length in above step (1): specifically, in order to ensure no effect on the anaerobic environment of the surface sediment, the water column is generally 10-50 cm long, so as to ensure no effect of surface water body on dynamic oxygen state of bottom water body. The water column which is 20-25 cm long is preferable.

Amount of 0.1% $HgCl_2$ used in above step (2) is usually 5~15 mL $HgCl_2$/kg sludge, and amount of dry ice used occupies more than ¾ of remaining volume above the sludge sample in the bottle.

In above steps (3) and (4), in order to ensure that volatile thio-ether compounds in the sediment is not subject to oxidative deterioration by air, the following sample extraction work is performed in an anaerobic environment, and the preferable device is a large indoor anaerobic operation chamber.

During alcohol/water exchange of the first step in above step (3), temperature of mixture shaking and centrifugation should be kept consistent, preferably the temperature is 10-15° C. The numerical value of solid-to-liquid ratio is preferably 1:2-1:5; above extractant is not limited to methanol, and can be replaced by ethanol. Concentration of added NaCl is 10-20% (W/V, NaCl/methanol).

During ultrasonic extraction with mixed extractant in the second step in above step (3), with respect to the sediment samples with different properties, the methanol/cyclohexane ratio of above extractant is 1:0.5-1:3, preferably 1:0.5-1:1, the solid-to-liquid ratio of extract is 1:2-1:3, and the temperature of ultrasonic extraction should be consistent with the extraction temperature of the first step. Time of ultrasonic extraction is preferably 10-30 min. The ultrasonic extraction instrument should be selected to have power greater than 800 w and frequency of 20 KHz.

Preferably the power is 900-1200 w. Extractant described above is not limited to methanol and can also be replaced by ethanol.

Filler of the above solid phase extraction column in above step (4) is C18 and XAD-16. Preferably with XAD-16 as the solid phase extraction filler, impurities are separated more thoroughly, and volatile thio-ether compounds have less influence on gas chromatogram. Absorbent cotton which is 2 cm long is placed on the lowest end of the solid phase extraction column, and then anhydrous sodium sulfate which is 2 cm long is filled on each of the upper end and the lower end for further dehydrating. It finds in the experiment that lower flow rate can reduce time of repeating column chromatography, but the effect of the flow rate on experimental results can be negligible, and impurities in the extract are separated and purified at a flow rate of 3-5 mL/min. The eluent is preferably ethyl acetate, and the flow rate of eluent is controlled to collect the eluent dropwise while eluting. The collected eluent is further concentrated on a rotary evaporator to 1-2 mL for determination, and then detected on a gas chromatograph or gas chromatograph-mass spectrometer.

In above step (4) the specific method for pre-treating the solid phase extraction filler C18 and XAD-16, as well as anhydrous sodium sulfate and absorbent cotton before loading onto a chromatography column is as follows:

XAD-16 pre-treatment: soaking with 95% ethanol for 24 h, then rinsing with deionized water until the eluent is mixed with water without white opacity, and washing with distilled water until there is no alcohol taste; adding 4% hydrochloric acid solution to soak resin for 5 h, then washing with distilled water to be neutral; soaking the resin for additional 5 h with 5% NaOH solution, and washing with distilled water to be neutral; performing suction filtration under a vacuum pump, until no water drops, for use;

C18 pre-treatment: rinsing with cyclohexane in the solid phase extraction column at 5 mL/min, and repeating 3 times for use;

pre-treatment with anhydrous sodium sulfate: baking in 500° C. high-temperature furnace for 4 h, collecting in a wide-mouth glass bottle after cooling down to room temperature, sealing and storing for use; and pre-treatment with absorbent cotton: refluxing with cyclohexane vapor for 16 h, taking out and drying in the air for use.

Beneficial effects of the invention: (1) the invention relates to collection and storage of samples, and can ensure, to the largest extent, that occurrence form, amount and categories of volatile thio-ether compounds in the bottom mud are original after leaving the water ecosystem. (2) The two-step continuous extraction method of the invention can synchronously extract and effectively purify a plurality of volatile thio-ether compounds in the sediment, while the determination spectra of samples during gas chromatography detection will not be subject to masking or overlapping interference of peaks of impurities. (3) The invention relates to selection of extraction temperature and time and ultrasonic power of the instrument, selection of the solid phase extraction column, and optimization of eluent, flow rate and many parameters during extraction and purification process of volatile thio-ether compounds, and to the largest extent, ensures a higher standard recovery rate of the samples, and the total standard recovery rate during the extraction process is 85-115%, which completely satisfies requirements of sample determination.

Technical advances of the invention: the invention relates to an extraction method of compounds such as dimethyl trisulfide in the sediment, which can rapidly and accurately extract most of components in the sediment, with a standard recovery rate of extraction being 85-114%, thus satisfying requirements of sample determination. The invention employs a high-efficient method of extracting volatile thio-ether compounds in the sediment, not only provides a complete solution of critical steps and extraction parameters in the extraction and purification process of the sediments with different properties, but also strictly controls system error of sulfide loss that may occur in the process, including shortening the extraction time as much as possible with the proviso of ensuring stable extraction rate, controlling the extraction temperature below 15° C., and substantially producing no volatilization of volatile thio-ether compounds. In contrast, traditional Soxhlet extraction needs nearly 48 h, the extraction process is significantly long, and loss risk of volatile volatile thio-ether compounds is increased, and standard recovery rate of the sample will be further decreased, which effects accuracy of determination. The method of the invention takes short time, shortens the extraction time to 15 min, and performs ultrasonic extraction at low temperature to greatly reduce possibility of volatilization loss of compounds to be determined in the extraction process.

DETAILED DESCRIPTION OF PARTICULAR EMBODIMENTS OF THE INVENTION

Figure 1:
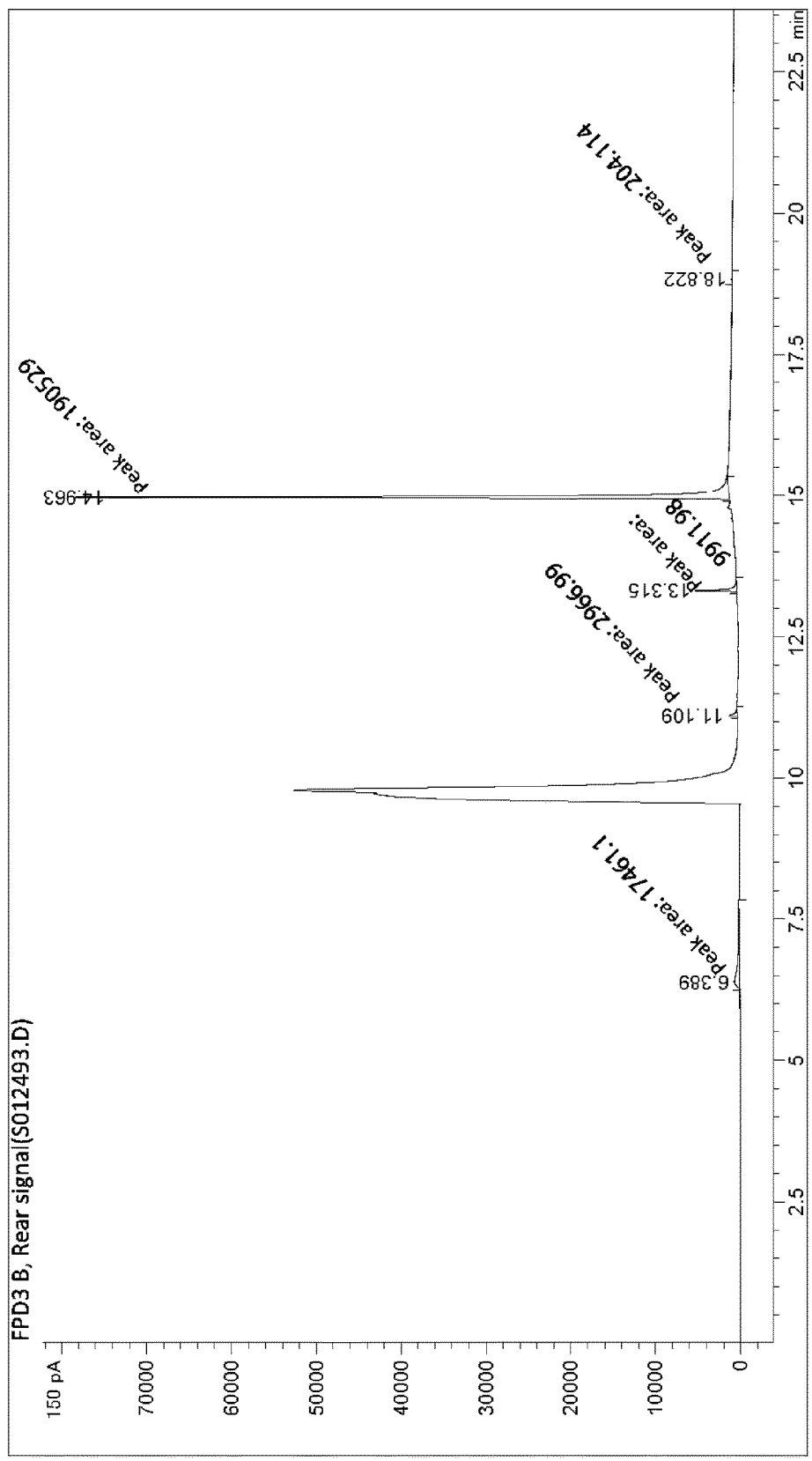
FIG. 1 is a gas chromatogram of categories and content of volatile thio-ether compounds in sediment in Cyanobacteria area of Meiliang Bay, Taihu Lake, wherein a is hydrogen sulfide, b is methanethiol, c is dimethyl sulfide, d is dimethyl disulfide, and e is dimethyl disulfide.

The technical schemes of the invention will be described in detail in conjunction with Embodiments and drawings. Protection scope of the invention is not limited by the detailed embodiment, but limited by the claims.

Embodiment 1

According to the invention, the extraction method of volatile thio-ether compounds in sediment sample collected in Cyanobacteria area of Meiliang Bay, Taihu Lake is as follows:

(1) Sample collection and sealed storage away from light: collecting a cylindrical core sample of fresh sediment from a lake or river bed by a sediment corer and retaining a water column which is 20 cm long, and removing stones, animal and plant residues such as snails, corbicula fluminea and plant root system in the sludge sample; collecting 0-10 cm fresh sludge samples on the surface, rapidly filling 30 g into a 50 mL brown glass bottle after mixing adequately and retaining water of about 1 cm, and then sealing.

(2) Sample refreshing and anaerobic pre-treatment: adding 5 mL of 0.1% $HgCl_2$ to the surface of fresh sediment for sterilization, adding 15 g of dry ice at the same time, finally placing the brown sample bottle into a liquid nitrogen container for cold storage, and transporting back to laboratory in time for determination.

(3) Volatile thio-ether compound extraction.

The first step: crude extraction: first weighing about 5 g sediment sample in a 50 mL centrifuge tube, adding absolute methanol and 10% NaCl solution at a solid-to-liquid ratio of 1:3, shaking adequately at 15° C., then centrifuging on a centrifuge at 5000 rpm at 15° C. for 10 min, collecting supernatant after standing still, repeating three times, and finally combing supernatant extracted three times above for use.

The second step: ultrasonic extraction with mixed extractant: adding 1:0.5 mixed extraction solution of methanol/cyclohexane to a residual sludge sample extracted in the first step at a solid-to-liquid ratio of 1:2, then performing ultrasonic extraction in an ultrasonic cell disruption instrument (power of ultrasonic intensity of the instrument is 900 w) at 15° C. for 15 min; then centrifuging on a centrifuge at 5000 rpm at 15° C. for 10 min, collecting supernatant after standing still, repeating three times, and finally combing supernatant extracted three times above for use.

(4) Purification of the extract: collecting and combing the extract obtained in the first step and the second step, further dehydrating with absorbent cotton carrying anhydrous sodium sulfate, and then purifying in the C18 solid phase extraction column, separating and purifying impurities in the extract at a flow rate of 5 mL/min; and finally eluting with 50 mL ethyl acetate solution, collecting the eluent at the flow rate of eluent being dropwise while eluting, and repeating three times; collecting the eluent and concentrating on a rotary evaporator to 1 mL for use and then determination.

The specific method for pre-treating C18 solid phase extraction column as well as anhydrous sodium sulfate and absorbent cotton before loading onto a chromatography column is as follows:

C18 solid phase extraction column pre-treatment: rinsing with cyclohexane in the solid phase extraction column at 5 mL/min, and repeating 3 times for use;

pre-treatment with anhydrous sodium sulfate: baking in 500° C. high-temperature furnace for 4 h, collecting in a wide-mouth glass bottle after cooling down to room temperature, sealing and storing for use; and pre-treatment with absorbent cotton: refluxing with cyclohexane vapor for 16 h, taking out and drying in the air for use.

(5) Sample determination: determining the concentrated solution to be determined on Agilent gas chromatograph, and specific determination condition of Agilent 7890A GC-FPD: loaded gas is high-purity He, at a flow rate of 3 mL/min; hydrogen flow rate: 50 mL/min; air flow rate: 65.0 mL/min; make-up flow rate (He): 30.0 mL/min; injection port temperature: 250° C.; splitless injection; detector temperature: 250° C.; initial column temperature is 50° C., kept for 5 min, increased at 20° C./min to 250° C. and kept for 7 min.

Through determination, FIG. 1 is distribution information of volatile thio-ether compounds in sediment in Cyanobacteria area of Meiliang Bay, Taihu Lake, and provides strong technical support for scientifically evaluating diffusion flux of volatile thio-ether compounds at the sediment-water interface.

Embodiment 2

According to the invention, the extraction method of volatile thio-ether compounds in sediment sample collected in reed wetland of Meiliang Bay, Taihu Lake is as follows:

(1) Sample collection and sealed storage away from light: collecting a cylindrical core sample of fresh sediment from a lake or river bed by a sediment corer and retaining a water column which is 22 cm long, and removing stones, animal and plant residues such as snails, corbicula fluminea and plant root system in the sludge sample; collecting 0-10 cm fresh sludge samples on the surface, rapidly filling 30 g into a 50 mL brown glass bottle after mixing adequately and retaining water of about 1 cm, and then sealing.

(2) Sample refreshing and anaerobic pre-treatment: adding 10 mL of 0.1% $HgCl_2$ to the surface of fresh sediment for sterilization, adding 15 g of dry ice at the same time, finally placing the brown sample bottle into a liquid nitrogen container for cold storage, and transporting back to laboratory in time for determination.

(3) Volatile thio-ether compound extraction.

The first step: crude extraction: first weighing about 5 g sediment sample in a 50 mL centrifuge tube, adding absolute ethanol and 20% NaCl solution at a solid-to-liquid ratio of 1:2, shaking adequately at 10° C., then centrifuging on a centrifuge at 5000 rpm at 10° C. for 10 min, collecting supernatant after standing still, repeating three times, and finally combing supernatant extracted three times above for use.

The second step: ultrasonic extraction with mixed extractant: adding 1:1 mixed extraction solution of methanol/cyclohexane to a residual sludge sample extracted in the first step at a solid-to-liquid ratio of 1:3, then performing ultrasonic extraction in an ultrasonic cell disruption instrument (power of ultrasonic intensity of the instrument is 1200 w) in 10° C. water bath for 10 min; then centrifuging on a centrifuge at 5000 rpm at 10° C. for 10 min, collecting supernatant after standing still, repeating three times, and finally combing supernatant extracted three times above for use.

(4) Purification of the extract: collecting and combing the extract obtained in the first step and the second step, further dehydrating with absorbent cotton carrying anhydrous sodium sulfate, and then purifying in the XAD-16 resin-filled solid phase extraction column, with a filling length of XAD-16 resin being 25 cm, separating and purifying impurities in the extract at a flow rate of 3 mL/min; and finally eluting with 50 mL ethyl acetate solution, collecting the eluent at the flow rate of eluent being dropwise while eluting, and repeating three times; collecting the eluent and concentrating on a rotary evaporator to 1 mL for use and then determination.

The solid phase extraction filler XAD-16 as well as anhydrous sodium sulfate and absorbent cotton are pre-treated before loading onto a chromatography column, and XAD-16 pre-treatment method is as follows:

soaking with 95% ethanol for 24 h, then rinsing with deionized water until the eluent is mixed with water without white opacity, and washing with distilled water until there is no alcohol taste; adding 4% hydrochloric acid solution to soak resin for 5 h, then washing with distilled water to be neutral; soaking the resin for additional 5 h with 5% NaOH solution, and washing with distilled water to be neutral; performing suction filtration under a vacuum pump, until no water drops, for use.

The pre-treatment method with anhydrous sodium sulfate and absorbent cotton is the same as in Embodiment 1.

(5) Sample determination: determining the concentrated solution to be determined on Agilent gas chromatograph, and specific determination condition of Agilent 7890A GC-FPD: loaded gas is high-purity He, at a flow rate of 3 mL/min; hydrogen flow rate: 50 mL/min; air flow rate: 65.0 mL/min; make-up flow rate (He): 30.0 mL/min; injection port temperature: 250° C.; splitless injection; detector temperature: 250° C.; initial column temperature is 50° C., kept for 5 min, increased at 20° C./min to 250° C. and kept for 7 min.

Figure 2:
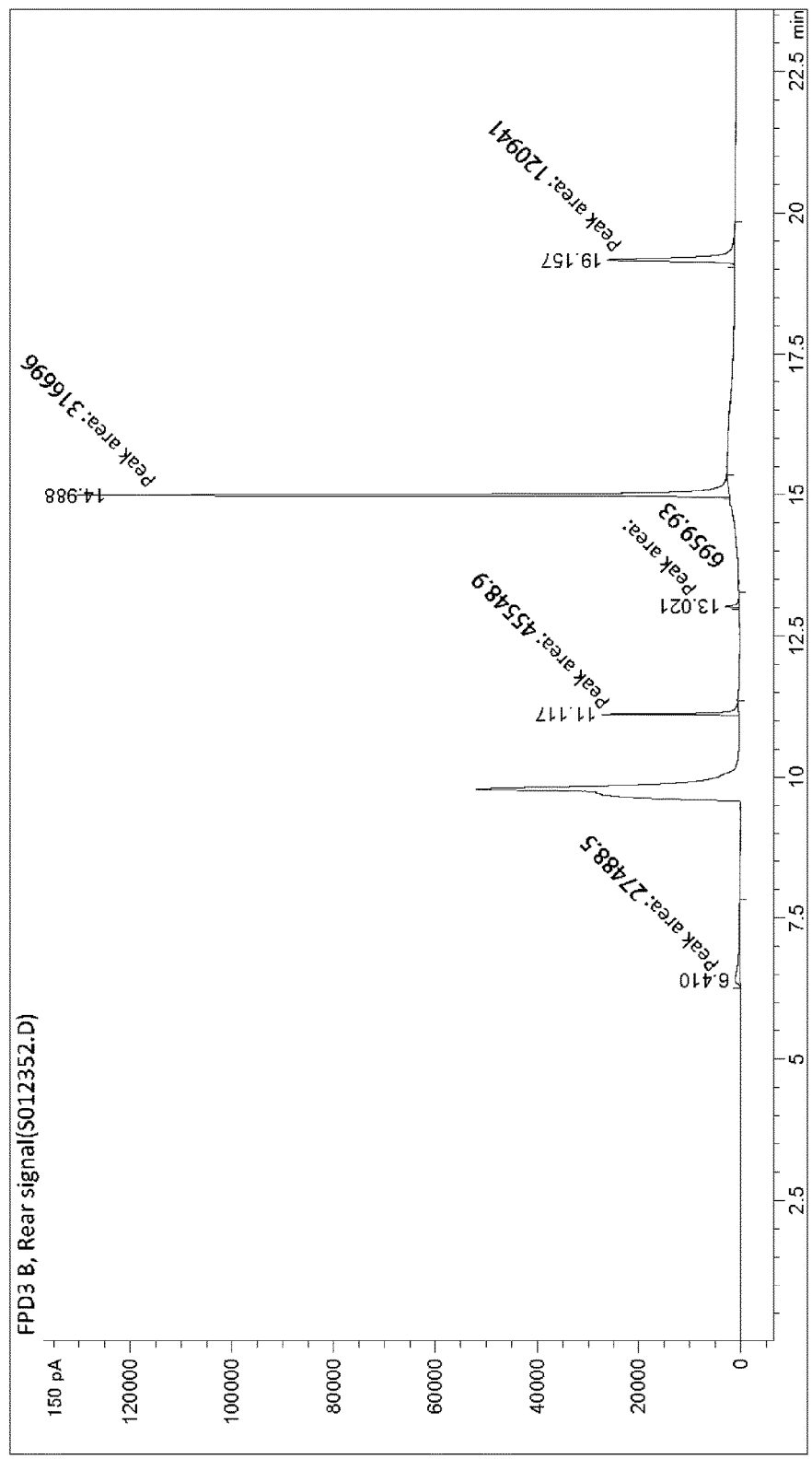
FIG. 2 is a gas chromatogram of categories and content of volatile thio-ether compounds in sediment in reed wetland of Meiliang Bay, Taihu Lake, wherein a is hydrogen sulfide, b is methanethiol, c is dimethyl sulfide, d is dimethyl disulfide, and e is dimethyl disulfide.

Through determination, FIG. 2 is distribution information of volatile thio-ether compounds in sediment in reed wetland of Meiliang Bay, Taihu Lake, and provides strong technical support for scientifically evaluating diffusion flux of volatile thio-ether compounds at the sediment-water interface.

Embodiment 3

By the technical scheme of the invention, the collected river bed sediment is subject to pre-treatment for extracting volatile thio-ether compounds:

(1) Sample collection and sealed storage away from light: collecting a cylindrical core sample of fresh sediment from a lake or river bed by a sediment corer and retaining a water column which is 25 cm long, and removing stones, animal and plant residues such as snails, *corbicula fluminea* and plant root system in the sludge sample; collecting 0-10 cm fresh sludge samples on the surface, rapidly filling 25 g into a 50 mL brown glass bottle after mixing adequately and retaining water of about 1 cm, and then sealing.

(2) Sample refreshing and anaerobic pre-treatment: adding 15 mL of 0.1% $HgCl_2$ to the surface of fresh sediment for sterilization, adding 15 g of dry ice at the same time, finally placing the brown sample bottle into a liquid nitrogen container for cold storage, and transporting back to laboratory in time for determination.

(3) Volatile thio-ether compound extraction.

The first step: crude extraction: first weighing about 5 g sediment sample in a 50 mL centrifuge tube, adding absolute methanol and 15% NaCl solution at a solid-to-liquid ratio of 1:5, shaking adequately at 12° C., then centrifuging on a centrifuge at 5000 rpm at 12° C. for 10 min, collecting supernatant after standing still, repeating three times, and finally combing supernatant extracted three times above for use.

The second step: ultrasonic extraction with mixed extractant: adding 1:3 mixed extraction solution of methanol/cyclohexane to a residual sludge sample extracted in the first step at a solid-to-liquid ratio of 1:2.5, then performing ultrasonic extraction in an ultrasonic cell disruption instrument (power of ultrasonic intensity of the instrument is 1200 w) at 12° C. for 30 min; then centrifuging on a centrifuge at 5000 rpm at 12° C. for 10 min, collecting supernatant after standing still, repeating three times, and finally combing supernatant extracted three times above for use.

(4) Purification of the extract: collecting and combing the extract obtained in the first step and the second step, further dehydrating with absorbent cotton carrying anhydrous sodium sulfate, and then purifying in the XAD-16 solid phase extraction column, with a filling length of XAD-16 resin being 25 cm, separating and purifying impurities in the extract at a flow rate of 4 mL/min; and finally eluting with 50 mL ethyl acetate solution, collecting the eluent at the flow rate of eluent being dropwise while eluting, and repeating three times; collecting the eluent and concentrating on a rotary evaporator to 1 mL for use and then determination.

The solid phase extraction filler XAD-16 as well as anhydrous sodium sulfate and absorbent cotton are pre-treated before loading onto a chromatography column, and the pre-treatment method is the same as in Embodiment 1.

(5) Sample determination: determining the concentrated solution to be determined on Agilent gas chromatograph, and specific determination condition of Agilent 7890A GC-FPD: loaded gas is high-purity He, at a flow rate of 3 mL/min; hydrogen flow rate: 50 mL/min; air flow rate: 65.0 mL/min; make-up flow rate (He): 30.0 mL/min; injection port temperature: 250° C.; splitless injection; detector temperature: 250° C.; initial column temperature is 50° C., kept for 5 min, increased at 20° C./min to 250° C. and kept for 7 min.

Figure 3:
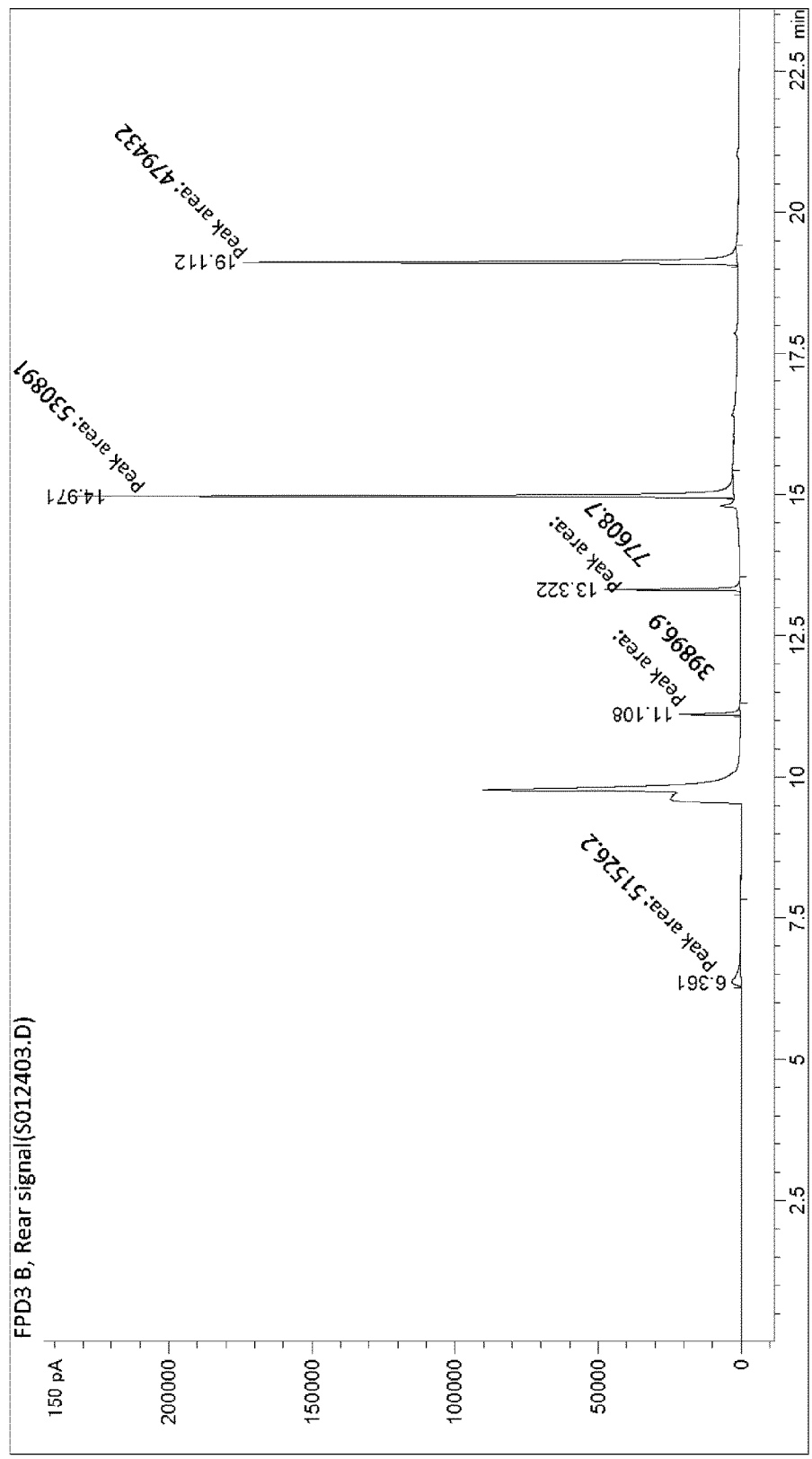
FIG. 3 is a gas chromatogram of categories and content of volatile thio-ether compounds in sediment in river bed of Wunan River, Changzhou, wherein a is hydrogen sulfide, b is methanethiol, c is dimethyl sulfide, d is dimethyl disulfide, and e is dimethyl disulfide.

Through determination, FIG. 3 is distribution information of volatile thio-ether compounds in sediment in river bed of Wunan River, Changzhou, and provides strong technical support for scientifically evaluating diffusion flux of volatile thio-ether compounds at the sediment-water interface. Through determination of volatile thio-ether compounds in river bed sediment, the vertical and horizontal distribution information of volatile thio-ether compounds in the sediment can be known in time, so as to provide technical support for further implementing ecological project and eliminating black and odorous problem of the river bed.

What is claimed is:

1. A pre-treatment method for the determination of volatile thio-ether compounds in offensive odorous sediment, comprising the following steps:
   (1) collecting a sample of an offensive odorous material and storage and storing the sample away from light in a brown bottle to allow it to form a fresh sediment with a surface;
   (2) adding 0.1% $HgCl_2$ to the surface of the fresh sediment for sterilization, while at the same time adding dry ice to keep the sample refrigerated, and create an anaerobic environment on the surface of the fresh sediment; and finally placing the sample into a liquid nitrogen container for cold storage;
   (3) extracting a volatile thio ether compound from the sample in a two-step continuous extraction process, comprising a first step of alcohol/water exchange and a second step of ultrasonic extraction with a mixed extractant, wherein the first step comprises repeating three times a procedure of first weighing some sediment sample in a centrifuge tube, adding absolute methanol and NaCl, or absolute ethanol and NaCl, so that a solid-to-liquid ratio of a resulting mixture with the sample is 1:2-1:5, shaking adequately, then centrifuging and collecting supernatant after standing still, and finally combing supernatant from the three repeated procedures for further use and keeping a residual sludge of the sample for use in the second step;

the second step comprises adding a mixed extraction solution of methanol/cyclohexane or ethanol/cyclohexane at a ratio of 1:0.5-1:3 to the residual sludge from the first step at a solid-to-liquid ratio of 1:2-1:3, then performing three repeats of an ultrasonic extraction in an ultrasonic cell disruption instrument, and finally combing ultrasonic extract obtained from the three repeated ultrasonic extractions; and (4) combing the combined supernatant of the first step of step (3) and the combined ultrasonic extract of the second step of step (3) to form a total extract dehydrating the total extract with absorbent cotton carrying anhydrous sodium sulfate, then applying the total extract to a solid phase extraction column at a flow rate of 3-5 mL/min; and finally eluting with an ethyl acetate solution and collecting an eluent, and concentrating the eluent on a rotary evaporator for determination.

2. The pre-treatment method according to claim 1, wherein in step (1) the sample is collected from a lake or river bed and stones, animal and plant residues are removed from the sample.

3. The pre-treatment method according to claim 1, wherein, amount of 0.1% $HgCl_2$ used in step (2) is 5-15 mL $HgCl_2$/kg sludge.

4. The pre-treatment method according to claim 1, wherein, extraction operation of step (3) is performed in an indoor anaerobic chamber.

5. The pre-treatment method according to claim 1, wherein, extraction temperature of volatile thio-ether compounds in step (3) is below 15, and extraction time is 10-30 min.

6. The pre-treatment method according to claim 1, wherein, concentration of NaCl added during alcohol water exchange in step (3) is 10~20% (W/V).

7. The pre-treatment method according to claim 1, wherein, ratio of methanol or ethanol to cyclohexane in the mixed extraction solution in step (3) is 1:0.5-1:1.

8. The pre-treatment method according to claim 1, wherein, power of ultrasonic extraction instrument in step (3) is 900 W-1200 W.

* * * * *